United States Patent

Menon et al.

Patent Number: 5,818,228
Date of Patent: Oct. 6, 1998

[54] MEASUREMENT OF THE RESIN CONTENT OF A COMPOSITE MATERIAL BY NUCLEAR MAGNETIC RESONANCE

[75] Inventors: Suresh M. Menon; Geoffrey A. Barrall, both of San Diego; Erik E. Magnuson, Cardiff by the Sea, all of Calif.

[73] Assignee: XXSYS Technologies, Inc., San Diego, Calif.

[21] Appl. No.: 848,535
[22] Filed: Apr. 28, 1997
[51] Int. Cl.⁶ ...................................................... G01V 3/00
[52] U.S. Cl. ............................................ 324/300; 324/307
[58] Field of Search ..................................... 324/300, 303, 324/306, 307, 309, 314, 318, 322

[56] References Cited

U.S. PATENT DOCUMENTS

| | | | |
|---|---|---|---|
| 4,532,218 | 7/1985 | Strom | 324/300 |
| 4,769,601 | 9/1988 | Herrick | 324/300 |
| 5,198,766 | 3/1993 | Spraul et al. | 324/300 |
| 5,302,897 | 4/1994 | Tache et al. | 324/300 |
| 5,321,358 | 6/1994 | Mohr et al. | 324/300 |

*Primary Examiner*—Louis M. Arana
*Attorney, Agent, or Firm*—Gregory Garmong

[57] ABSTRACT

The resin content of an organic resin-matrix composite material is measured nondestructively by nuclear magnetic resonance. A specimen of the composite material is placed into a constant magnetic field and subjected to a radio-frequency magnetic field pulse. The response of the material is indicative of the amount of organic resin that is present. The response may be used as a feedback signal to control the operation of a manufacturing machine.

17 Claims, 4 Drawing Sheets

○ SPOOL 2 #4
△ SPOOL 9 #1
▽ SPOOL 9 #3
▼ SPOOL 12 #4

MEASUREMENT OF THE RESIN CONTENT OF A COMPOSITE MATERIAL BY NUCLEAR MAGNETIC RESONANCE

This invention was made with United States Government support under cooperative agreement number 70NANB5H1051 awarded by National Institute of Standards and Technology. The United States Government has certain rights in the invention.

BACKGROUND OF THE INVENTION

This invention relates to the nondestructive measurement of the amount of resin present in a composite material having an organic resin matrix.

One type of composite material includes a reinforcement phase embedded within a matrix phase. Unlike an alloy, each phase retains its physical identity in the composite material. The reinforcement may be hard, strong fibers, such as carbon, graphite, glass, or kevlar fibers. Many different types of matrix materials are known, and in one widely used composite material the matrix is an organic resin such as an epoxy, a polyester, or a polyimide. The properties of the composite material reflect the high strength or elastic modulus of the reinforcement fibers, while the matrix binds the reinforcement fibers together and imparts toughness.

Composites of reinforcing fibers in an organic resin matrix may be manufactured by solution coating, hot melt processing, or otherwise applying an uncured resin matrix to bundles of the fibers, either in batch form or, preferably, continuously. The resin is slightly cured (i.e., B-staged) or hardened during manufacturing of this initial composite material, so that it is solid and no longer a fluid. The resulting material, termed a prepreg, is provided to the manufacturers of final articles who make parts from the material. The prepreg is pliable and readily arranged onto forms. Parts are made by collating plies of the prepreg onto a form or in a mold in a desired arrangement, and then further curing the resin phase of the composite material under heat and pressure.

The properties of the final part and some of the manufacturing procedures are highly dependent upon the amounts of fiber and organic resin material present in the composite material. Designers and manufacturing engineers typically specify the weight or volume fractions of the phases of the composite material to within about plus-or-minus one percent. Manufacturing the prepreg material to these tolerances, with exactly the right amounts of fiber phase, resin matrix phase, and sizing, can be difficult, particularly because the resin is initially a viscous liquid whose exact amount and flow are hard to control.

A prerequisite to controllably manufacturing such composite materials to tight tolerances is the ability to determine the amounts of the phases accurately, rapidly, and concurrently with the manufacturing operation. Conventional destructive measurements of specimens to ascertain the amounts of the phases are usually accurate, but they are slow, expensive, and may require the use of dangerous or toxic solvents. Attempts have been made to apply nondestructive techniques such as ultrasonic wave methods, beta gages, and gamma gages to the measurement of the amounts of the phases. These methods have limited sensitivity and accuracy. Additionally, the inventors have recognized that the results obtained by these techniques are affected by the amounts of the phases, the nature of the reinforcement, the state of cure of the resin matrix phase, the temperature, and anomalies in the structure.

Thus, there is a need for an apparatus and an approach for nondestructively and rapidly determining the amounts of the phases in the composite material as it is manufactured, so that this information may be used in a feedback controller to continuously adjust the manufacturing machinery. The present invention fulfills this need, and further provides related advantages.

SUMMARY OF THE INVENTION

The present invention provides a nondestructive method and apparatus for measuring the amount of organic resin phase present in a composite material. The measurement recognizes and is responsive to the properties of the resin phase, so that the character, arrangement, wetting, and other properties of the reinforcement phase do not corrupt the results. The measurement may be conducted with a stationary specimen of the composite material or a moving specimen. The composite material may be a prepreg as it is being manufactured, and the resulting information may be used to control the prepreg manufacturing machinery. The technique is applicable to other states of the composite material as well, such as cured laminates.

In accordance with the invention, a method for determining an organic content of a specimen of a composite material having an organic resin matrix comprises the steps of providing a specimen of a composite material comprising a phase made of an organic resin material, performing a $^1$H nuclear magnetic resonance (NMR) measurement of the specimen to provide a measured NMR response, and associating the measured NMR response with the organic content of the phase of the specimen. The phase of most interest is the organic resin matrix. In a preferred form of the NMR measurement, the specimen is placed into a measurement apparatus having a constant-field magnet that generates a constant and uniform magnetic field, and a variable-field coil that may be excited by a radio frequency signal. The method includes applying a constant magnetic field to the specimen with the constant-field magnet, perturbing the magnetic field applied to the specimen with a radio frequency magnetic field produced by passing a radio frequency current through the variable-field coil, while the constant magnetic field is applied, and measuring the measured NMR response of a resulting current induced in the variable-field coil by the specimen. The results may be correlated with prior calibration relations between the nuclear magnetic resonance response and the amount of the resin present, to allow a determination of the amount of the resin phase present in an unknown specimen.

The NMR measurement is sensitive primarily to the properties of the organic phase(s), and in particular primarily to the chemical composition and amount of the organic phase(s). The NMR measurement is relatively insensitive to the fiber materials such as carbon fiber, graphite fiber, or glass fiber. If the composition is maintained constant, as is normally the case for the mass production of prepreg material, the NMR measurement of the organic resin matrix phase is a direct indicator of the amount of resin present within a measurement volume. The nuclear magnetic resonance measurement may therefore be used to determine the relative amounts of resin matrix material and fiber present in the composite material. The accuracy obtained in initial studies on the order of about one-percent by weight of resin content, which is sufficient for most applications.

The approach of the invention may be used for stationary measurements of resin content, or for measurements where the composite material is moving through the measurement volume. Each measurement requires about 200 milliseconds or less, and it is preferred to average several measurements for improved accuracy. For prepreg material typically produced by manufacturing apparatus at a rate of about 12–25 feet per second, this measurement rate permits substantially continuous monitoring of resin content in the prepreg material as it is manufactured. The nuclear magnetic resonance measurement may be used as a feedback signal for control of the relative amounts of reinforcement and matrix material fed to the manufacturing apparatus.

The approach of the invention may also be used to determine the relative state of cure or hardness of the organic resin. For example, the composite material may be slightly cured (i.e., B-staged) or hardened prior to or during manufacture. The measurement of the invention contains information in the rate of decay of the measured response which is sensitive to the relative molecular mobility of the organic resin where the molecular mobility of the organic resin is a prime indicator of the state of cure or hardness of the resin, or the resin content of cured laminates.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
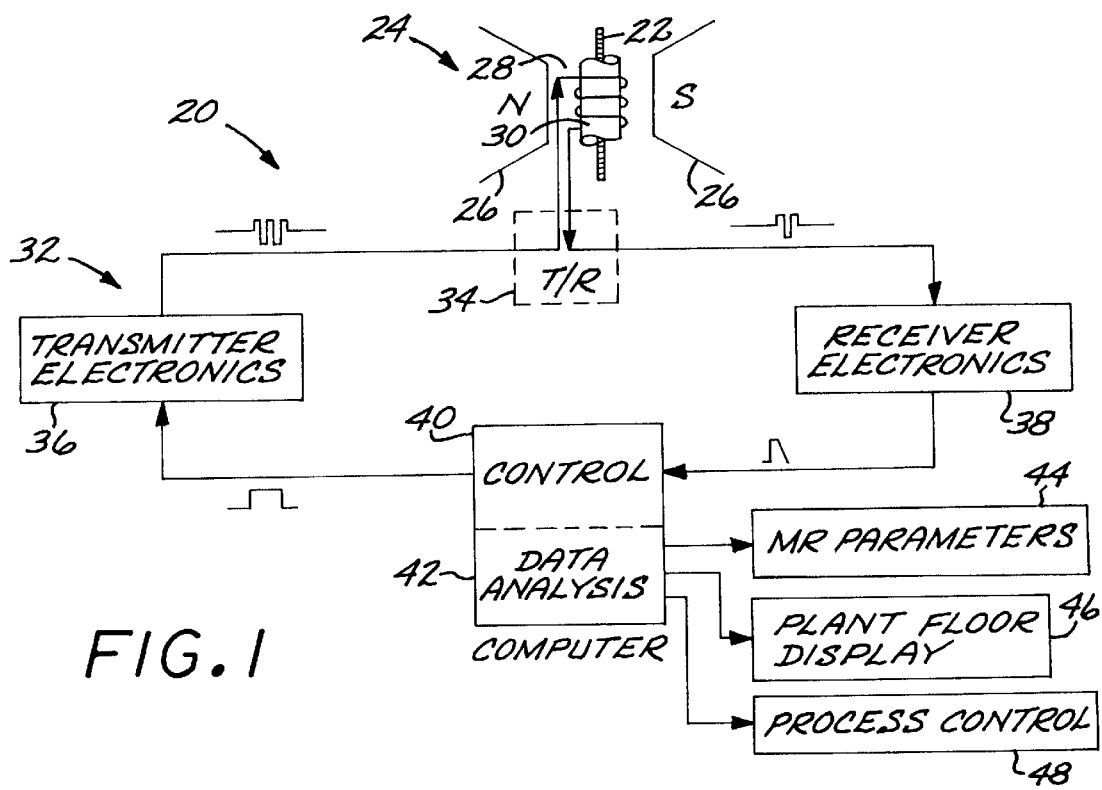
FIG. 1 is a schematic diagram of a nuclear magnetic resonance measurement apparatus.

FIG. 1 illustrates a nuclear magnetic resonance (NMR) measurement apparatus 20 used to determine the amount of resin in a specimen 22 of composite material. The specimen 22 may be any operable composite material with an organic resin phase. In a typical case, the composite material has reinforcement embedded in an organic resin matrix, optionally with a sizing present on the surface of the reinforcement. The resin matrix may be in a partially cured (as in a prepreg) or fully cured state, or it may even be in a fully uncured fluid state. (As used herein, "uncured" includes both fully uncured and partially cured states.) The reinforcement may be of any operable type or geometry. The reinforcement may be, for example, carbon fibers, graphite fibers, or glass fibers. Organic reinforcement such as kevlar fibers may also be used, but their effect must be separated from the effect of the other organic phases present. The reinforcement may be of any geometry, for example particulate or fibrous.

Nuclear magnetic resonance theory, techniques, and measurement apparatus are well known for use in other applications, see, for example, A. Abragam, *Principles of Nuclear Magnetism*, Oxford: Clarendon Press, 1961. The following discussion describes a preferred NMR apparatus for use in the present invention. A measurement head 24 of the NMR measurement apparatus 20 includes a constant-field magnet 26, which typically is a permanent magnet, with north and south poles and a measurement volume 28 therebetween. A variable-field coil 30 is positioned within the measurement volume 28. The variable-field coil 30 is of sufficient diameter to receive the specimen 22 therein. The specimen 22 may be stationary within the variable-field coil 30 during a measurement, or the specimen may be moved through the variable-field coil 30 during a measurement. For an NMR apparatus 20 operable with the present invention and used to make the measurements described subsequently, the permanent magnet 26 has a field strength of about 2000 Gauss. The solenoidal copper variable-field coil 30 is about 2 centimeters in inside diameter and about 3.5 centimeters long. The variable-field coil is excited at a radio frequency excitation frequency of about 8.5 MHZ (megahertz). The applicability of the invention is not limited to this presently preferred NMR apparatus.

An electronics and control package 32 is connected to the variable-field coil 30. The electronics and control package 32 includes a transmit/receive switch 34 that passively or actively switches the variable-field coil 30 between the transmitter electronics 36 and the receiver electronics 38. The transmitter electronics 36 transmits a radio frequency excitation signal through the variable-field coil 30, producing a pulsed radio frequency magnetic field that perturbs the steady-state magnetic field produced by the magnet 26 within the measurement volume 28. In the apparatus described above, the duration of the radio frequency pulse is about 3 microseconds, the radio frequency field intensity is about 20 Gauss, and the input power is about 25 watts.

The magnet 26 aligns the magnetic moments of the $^1$H nuclei in the organic resin material. The pulsed magnetic field produced by the radio frequency excitation of the variable-field coil 30, perturbs the magnetic moments of the $^1$H nuclei from their aligned state. The switch 34 is operated to switch the variable-field coil 30 to the receiver electronics 38, so that the variable-field coil 30 acts as a detector of the oscillating magnetic field produced by the $^1$H nuclei. The oscillating magnetic field of the $^1$H nuclei imparts an oscillating voltage in the variable-field coil 30. For a composite material wherein the resin matrix material has an unchanging composition, the magnitude of the measured response amplitude depends upon the amount of resin present in the specimen.

The transmitter electronics 36 and the receiver electronics 38 are controlled by a controller 40. The receiver electronics 38 amplifies the oscillating voltage response of the variable-field coil 30, shifts the amplified signal in frequency to approximately zero frequency, and digitizes the signal. This output is provided to a data analysis computer 42.

The data analysis computer 42 processes the digitized signal to obtain the information for the organic phases as discussed subsequently. The computer may also, and preferably does, average a number of individual measurements to obtain an averaged value that reduces the effects of noise.

As will be discussed more fully subsequently, the analysis of the data leads to a value for the resin content of the composite specimen 22. This value may be stored as NMR parameters for future reference, numeral 44, output as a display, numeral 46, or used in process control, numeral 48.

Figure 2:
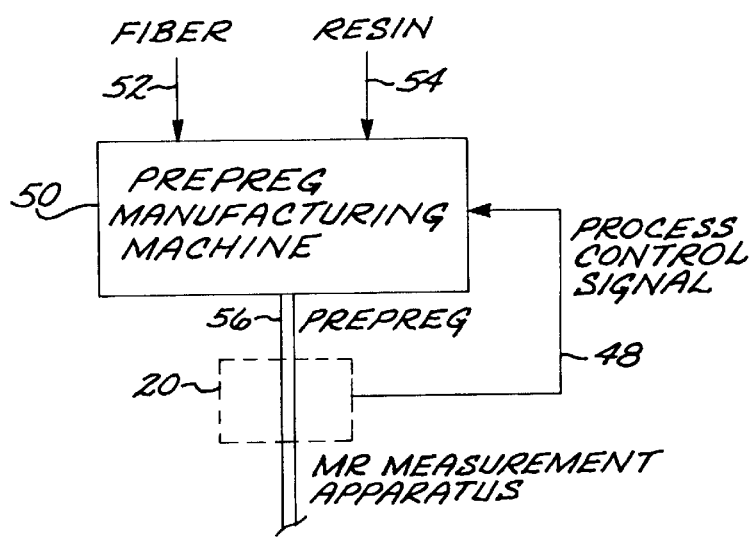
FIG. 2 is a schematic diagram of the use of the apparatus of FIG. 1 for prepreg-manufacture process control.

FIG. 2 illustrates the use of the present invention for process control applications in the production of a prepreg composite material. The prepreg material is made by a prepreg manufacturing machine 50. A number of such machines are known in the art, and the present approach may be used with any such machine wherein the amounts of the input reinforcement and organic matrix material may be varied. The machine 50 utilizes controllable amounts of input reinforcement fiber material 52 and input resin material 54 to produce a continuous output flow of prepreg material 56. The prepreg material that continuously moves from the machine 50 is passed through the measurement head 24 of the apparatus 20 of FIG. 1, producing the process control signal 48. The process control signal 48 is provided to the control portion of the machine 50 as a control signal, causing the relative amounts of the input reinforcement fiber material 52 and the input resin material 54 to be increased or decreased as necessary responsive to a desired set point level. In a typical prepreg manufacturing operation, the continuous rate of movement of the prepreg material 56 is about 12–25 feet per minute, which allows the feedback control system to maintain the resin content to within a tolerance of under about 1 percent variation.

Figure 3:
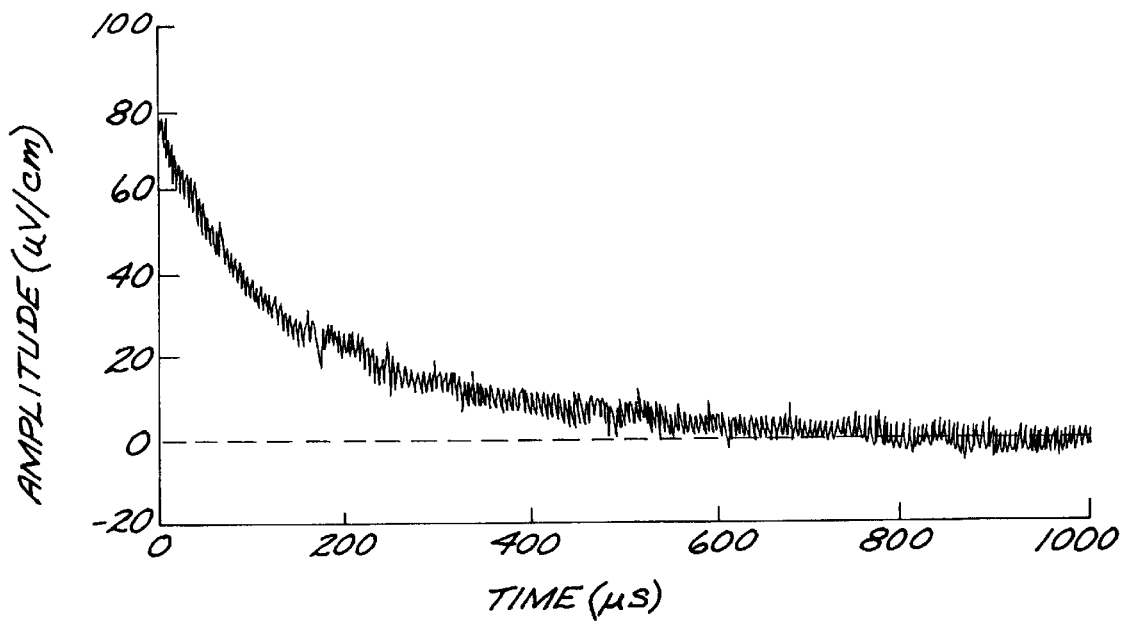
FIG. 3 is a graph of NMR response amplitude as a function of time during a nuclear magnetic resonance measurement.

FIG. 3 is a typical measured data output from the receiver electronics 38, showing the measured response amplitude as a function of time after the end of the perturbation pulse produced by the transmitter electronics 36. The stationary specimen was a 2.8 meter long piece of prepreg material made by Thiokol Corporation, having bundles of about 50,000 carbon fibers in an uncured epoxy organic resin matrix. The original state is restored in about 200 milliseconds, so that the next excitation signal may be initiated about 200 milliseconds after the prior excitation signal. The measured response amplitude is determined from the curve of FIG. 3 by any of several approaches performed by the computer 42. These approaches include, for example, extrapolating the curve of FIG. 3 back to 0-time, measuring the maximum amplitude of the NMR response, measuring the amplitude of the first point of the acquired data set, and fitting the Fourier transform of the NMR response to an appropriate model function such as a Lorentzian or Gaussian line shape.

Figure 4:
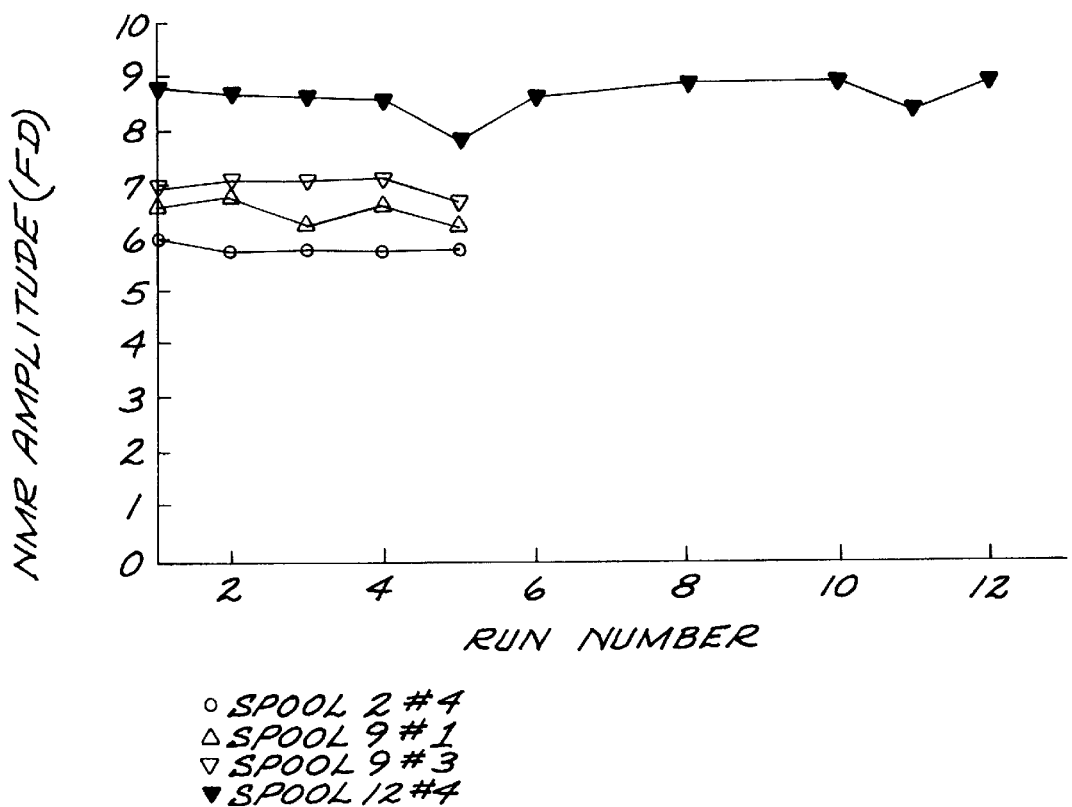
FIG. 4 is a graph of NMR response amplitude as a function of the number of the measurement.

FIG. 4 depicts the results of measurements made on four different specimens of a different composite prepreg material made by Hexcel Corporation, having bundles of about 12,000 carbon fibers in an uncured epoxy organic resin matrix. The vertical axis is the relative measured response amplitude, and the horizontal axis the test number of the repeated measurement on the same specimen. The results are generally quite repeatable. Because the NMR measurements are performed nondestructively and only a few tenths of a second apart, it is preferred to average a number of the individual measurements as shown in FIG. 4 to obtain an averaged measured response amplitude for use in subsequent computations. The averaged measured response amplitude results in improved accuracy in the final values.

Figure 5:
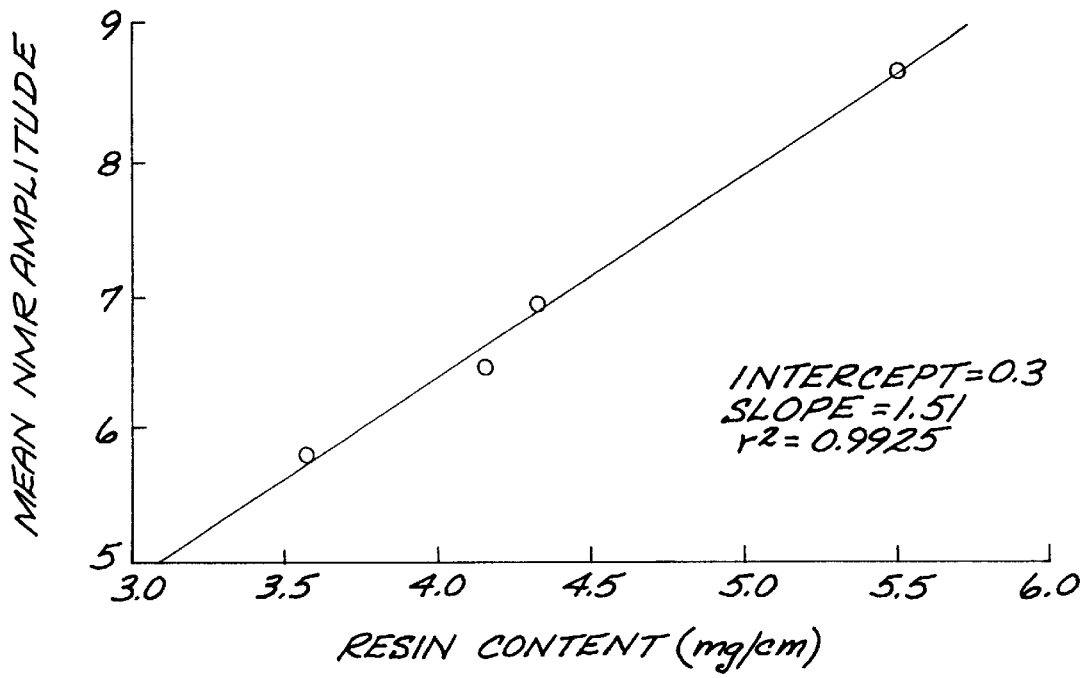
FIG. 5 is a correlation of NMR response amplitude as a function of resin content for a composite material.

The measured response amplitude or other feature of FIG. 3 may itself be used directly as the basis for process control or the like. In other cases, it is desired to convert that information to an actual resin content value. FIG. 5 is a calibration relationship for the Hexcel material discussed above, which may be used to convert the measured response amplitude, or, preferably, the averaged measured response amplitude, to a resin content. In an initial calibration study, a number of composite specimens having different resin contents were measured nondestructively using the approach detailed herein to obtain measured response amplitudes, with several measurements of the same specimen preferably averaged. The same specimens were thereafter evaluated destructively to obtain the actual value of the resin content, using known techniques such as solvent dissolution wherein the specimen is weighed, the resin is dissolved away using a solvent, and the remaining reinforcement is weighed. The value of the nondestructively measured NMR response amplitude is plotted against its destructively measured value, as shown in FIG. 5. This calibration relation is thereafter used as a resource for the determination of the resin contents of unknown specimens. From this calibration graph (or its mathematical expression) and the nondestructively measured NMR response amplitude for an unknown specimen, the numerical value of the resin content of the unknown specimen may be quickly established.

A translation apparatus was built and used with the measurement apparatus of FIG. 1 to obtain information on moving prepreg material, such as would be measured in the device of FIG. 2. A length of the Thiokol material discussed above was joined at its ends and moved through the measurement apparatus of FIG. 1 in a "fan belt" configuration, in order to evaluate whether successive measurements of a single length of moving material were reproducible. Successive measurements exhibited a maximum variation of only about 0.02 from the mean, which translates into a variation in measured resin content of less than about 0.6 percent (for a specimen having about 30 weight percent of organic resin material). The organic resin content was established using correlations such as shown in FIG. 5 (but determined for the Thiokol material).

In some cases, the fiber component of the composite material specimen may contain $^1H$ nuclei which contribute to the measured NMR response. $^1H$ nuclei are present in considerable quantity in fiber materials such as kevlar and in smaller quantity in incompletely carbonized carbon fiber. If the $^1H$ NMR response of the fiber is sufficiently large, the $^1H$ NMR response of the fiber may be removed by subtracting the NMR response of the bare fiber from the response of the composite material. The NMR response of the bare fiber may be determined either offline or in an online measurement prior to the NMR content measurement.

Figure 6:
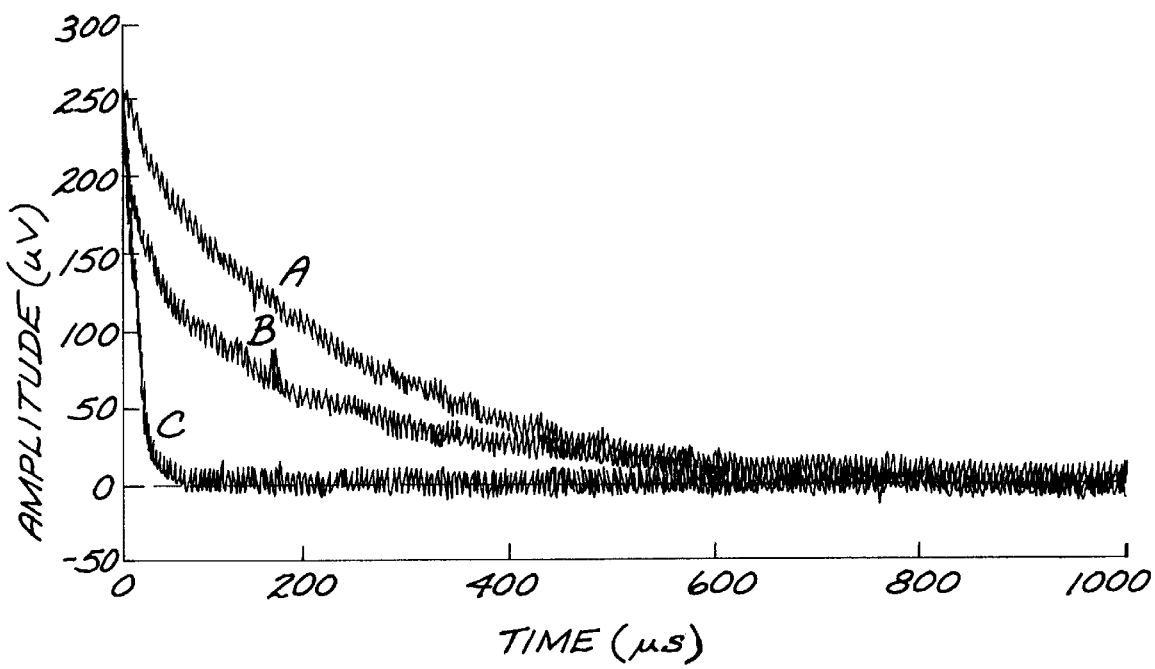
FIG. 6 is a graph of NMR response amplitude as a function of time for three different states of cure of an organic resin material.

The NMR response of the organic resin contains information which is sensitive to the state of cure or hardness of the resin. Following the NMR excitation, the NMR response decays with a characteristic time constant. The rate of decay is primarily determined by the molecular mobility of the organic resin. Resin which is more cured or hardened will decay more rapidly as illustrated in FIG. 6. FIG. 6 shows the NMR response of the organic resin for three different states of cure: A, the uncured material; B, the partially cured material; and C, the fully cured material. The rate of decay of the NMR response may be determined by a number of approaches such as fitting the data with a single exponential decay or multiple exponential decay model. The decay rate(s) or decay time constant(s) determined from the fit are then used as a measure of the resin cure or hardness.

Figure 7:
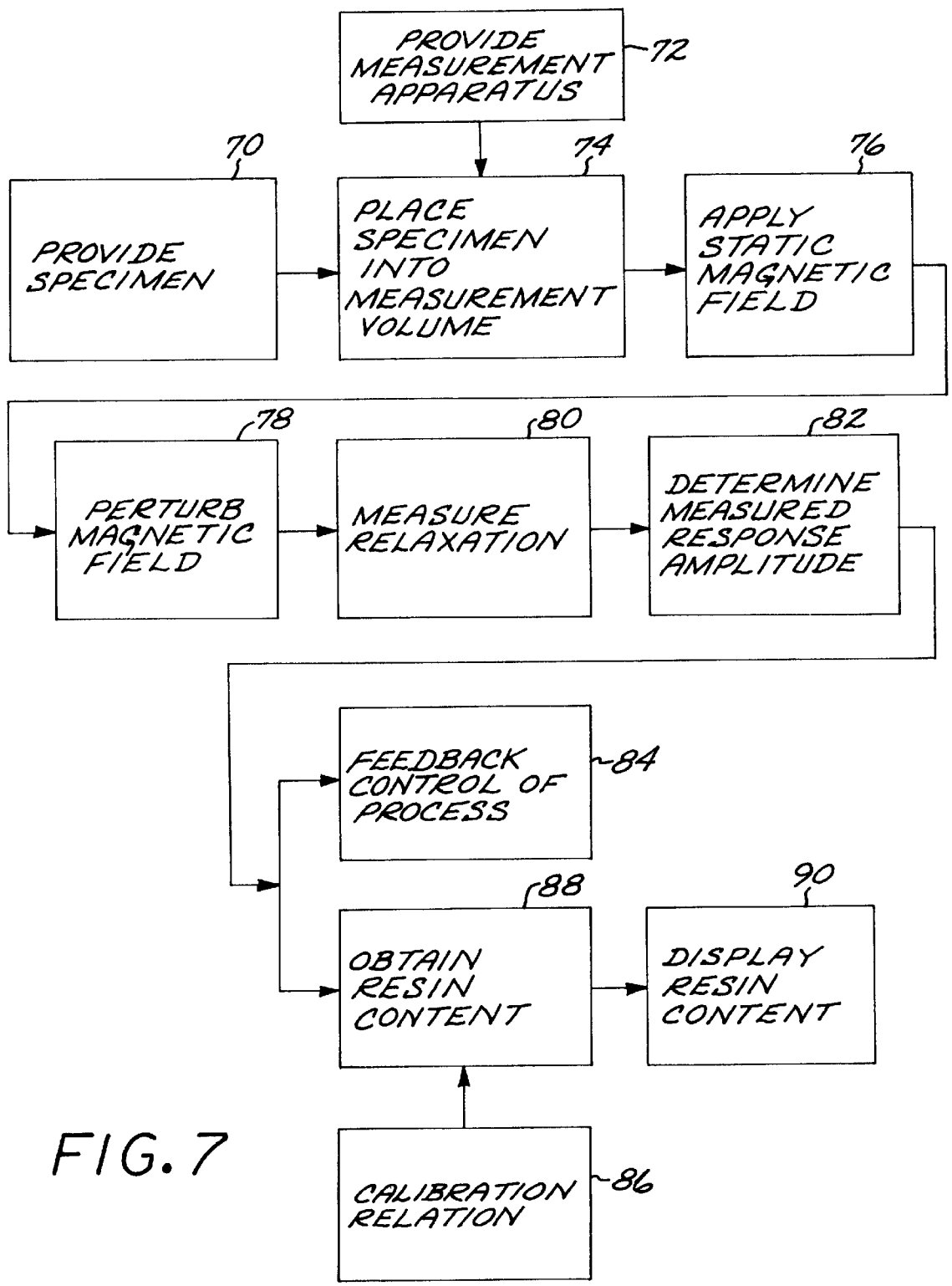
FIG. 7 is a block flow diagram of the practicing of the invention.

FIG. 7 summarizes the methodology of the present invention, according to the prior discussion. A specimen of a composite material having an organic resin matrix is provided, numeral 70. A nuclear magnetic resonance measurement apparatus is provided, numeral 72. The specimen is placed into the measurement volume of the measurement apparatus, numeral 74. The specimen may be either stationary within or moving through the measurement volume. A constant magnetic field is applied to the specimen in the measurement volume, numeral 76, and then the magnetic field is perturbed by a pulsed magnetic field, numeral 78.

The relaxation of the magnetically perturbed atoms is measured and recorded, numeral 80, and the measured response amplitude, decay rate, or other information of interest is determined from the measurement, numeral 82. This information may be used in any of several ways. It may be used directly for control purposes, as in feedback control, numeral 84. It also may be used, in conjunction with a previously determined calibration relation, numeral 86, to determine the actual resin content or state of cure, numeral 88. The actual resin content, in terms of a weight or percentage, may then be displayed, numeral 90.

The present invention has been practiced using the apparatus of FIG. 1, to obtain the results of FIGS. 3–6. The results indicate that the nuclear magnetic resonance measured response amplitude is a linear function of resin content in this case.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method for determining an amount of an organic resin matrix present in a specimen of a composite material, comprising the steps of:

providing a specimen of a composite material having an organic resin matrix;

applying a constant magnetic field to the specimen;

perturbing the magnetic field applied to the specimen with a pulsed variable radio frequency magnetic field, while the constant magnetic field is applied;

measuring a measured response amplitude of a resulting output produced by the specimen; and associating the measured response amplitude with the amount of the organic resin of the matrix of the specimen.

2. The method of claim 1, wherein the step of providing includes the step of providing a specimen of a prepreg composite material.

3. The method of claim 1, wherein the step of providing includes the step of providing a specimen of a prepreg composite material having carbon fibers embedded in an uncured resin matrix.

4. The method of claim 1, wherein the step of providing includes the step of providing a specimen of a cured composite material.

5. The method of claim 1, wherein the step of providing includes the step of continuously moving the specimen through a measurement region as the step of applying, perturbing, and measuring are performed.

6. The method of claim 1, wherein the step of applying includes the step of placing the specimen between the poles of a magnet having a constant magnetic field.

7. The method of claim 6, wherein the step of measuring includes the step of measuring the response in the coil of wire as a function of time.

8. The method of claim 1, wherein the step of perturbing includes the steps of providing a coil of wire connected to a controllable source of a radio frequency signal;

placing the specimen into the coil; and pulsing the coil with a radio frequency signal from the source of the radio frequency signal.

9. The method of claim 1, wherein the step of associating includes the steps of providing a calibration relation of measured response as a function of resin amount as prepared from calibration specimens of varying resin amounts; and comparing the measured response for the specimen with the calibration relation.

10. A method for determining a resin amount present in a specimen of a composite material comprising an organic resin matrix, comprising the steps of:

providing a specimen of a composite material having an organic resin matrix;

performing a nuclear magnetic resonance measurement of the specimen to provide a measured nuclear magnetic resonance response; and associating the measured nuclear magnetic resonance response amplitude with the amount of the resin present in the specimen.

11. The method of claim 10, wherein the step of performing includes the steps of placing the specimen into a measurement apparatus, the apparatus comprising
        a constant-field magnet having a constant magnetic field output, and
        a variable-field coil;

applying a constant magnetic field to the specimen with the constant-field magnet;

perturbing the constant magnetic field applied to the specimen with a pulsed variable magnetic field produced by passing a pulsed radio frequency current through the variable-field coil, while the constant magnetic field is applied; and measuring a measured nuclear magnetic resonance response of a resulting output induced in the variable-field coil by the specimen.

12. The method of claim 10, wherein the step of providing includes the step of providing a specimen of a prepreg composite material.

13. The method of claim 10, wherein the step of providing includes the step of providing a specimen of a prepreg composite material having carbon fibers embedded in an uncured resin matrix.

14. The method of claim 10, wherein the step of associating includes the steps of providing a calibration relation of measured nuclear magnetic resonance response as a function of the amount of resin present, prepared using calibration specimens of varying resin amounts; and comparing the measured nuclear magnetic resonance response amplitude for the specimen with the calibration relation.

15. A method for determining an amount of an organic material present in a phase of a specimen of a composite material comprising an organic material, comprising the steps of:

providing a specimen of a composite material having a phase comprising an organic material;

applying a constant magnetic field to the specimen;

perturbing the magnetic field applied to the specimen with a pulsed variable magnetic field, while the constant magnetic field is applied;

measuring a measured response amplitude of a resulting output induced by the specimen; and associating the measured response amplitude with the amount of the organic material present in the phase of the specimen.

16. The method of claim 15, including an additional step, after the step of associating, of controlling a prepreg manufacturing machine responsive to the organic amount of the phase present in the specimen as determined in the step of associating.

17. A method for controlling the operation of a machine for manufacturing a prepreg composite material having an organic resin matrix, comprising the steps of providing a manufacturing machine which manufactures a prepreg composite material having a reinforcement and an organic resin matrix;

producing a prepreg composite from input reinforcement material and input organic resin material, using the manufacturing machine;

applying a constant magnetic field to the prepreg composite material as it leaves the manufacturing machine;

perturbing the magnetic field applied to the prepreg composite material with a pulsed variable magnetic field, while the constant magnetic field is applied;

measuring a measured response amplitude of a resulting output induced by the prepreg composite material; and controlling the relative amount of input reinforcement material and input organic resin material used in the step of producing responsive to the measured response amplitude.

* * * * *